(12) United States Patent
Xu et al.

(10) Patent No.: US 8,173,007 B2
(45) Date of Patent: May 8, 2012

(54) HIGH TEMPERATURE ELECTROCHEMICAL CHARACTERIZATION OF MOLTEN METAL CORROSION

(75) Inventors: Jing Xu, Niederschsen (DE); Xingbo Liu, Morgantown, WV (US); Yinglu Jiang, Morgantown, WV (US); Frank Goodwin, Chapel Hill, NC (US)

(73) Assignee: West Virginia University, Morgantown, WV (US)

( * ) Notice: Subject to any disclaimer, the term of this patent is extended or adjusted under 35 U.S.C. 154(b) by 925 days.

(21) Appl. No.: 12/128,954

(22) Filed: May 29, 2008

(65) Prior Publication Data
US 2009/0101522 A1    Apr. 23, 2009

Related U.S. Application Data

(60) Provisional application No. 60/932,098, filed on May 29, 2007.

(51) Int. Cl.
*G01N 17/02* (2006.01)
*G01N 27/06* (2006.01)

(52) U.S. Cl. ......... 205/777; 204/404; 204/422; 324/700
(58) Field of Classification Search .......... 204/400–420, 204/421, 422; 205/776.5, 777; 324/425, 324/693, 700; 266/200
See application file for complete search history.

(56) References Cited

U.S. PATENT DOCUMENTS

| 4,601,810 A * | 7/1986 | Tiwari et al. ................... 204/413 |
| 5,393,400 A | 2/1995 | Yamaguchi et al. |
| 5,589,291 A | 12/1996 | Carlin et al. |
| 6,503,292 B2 * | 1/2003 | Klingensmith et al. ......... 75/386 |
| 6,693,443 B2 | 2/2004 | Ludwig et al. |
| 6,902,661 B2 * | 6/2005 | Thomas et al. ............. 205/776.5 |
| 2006/0012293 A1 | 1/2006 | Warner et al. |
| 2006/0257682 A1 | 11/2006 | Song et al. |

* cited by examiner

*Primary Examiner* — Kaj K Olsen
*Assistant Examiner* — Kourtney R Salzman
(74) *Attorney, Agent, or Firm* — Buchanan Ingersoll & Rooney PC; Craig G. Cochenour; Michael L. Dever (57) ABSTRACT

A system and method for the high temperature in-situ determination of corrosion characteristics of a molten metal on an alloy under study is provided which takes place within an insulated furnace. A graphite crucible provided in the furnace contains an electrolyte formed from a molten salt of a metal halide. A reference electrode formed from the same metal as the electrolyte is immersed in the electrolyte solution in the graphite crucible. A beta-alumina crucible containing a molten metal is also provided within the furnace and preferably within the graphite crucible. A measuring electrode formed from the alloy under study is immersed in the molten metal. Standard electrochemical techniques are used to measure and analyze the electrochemical effects of corrosion of the molten metal on the alloy.

17 Claims, 8 Drawing Sheets

Figure 3 a: original experimental result b: low frequency part corresponding to Warburg resistance

Figure 3 c: Warburg resistance fitting part I

Figure 3 d: Warburg resistance fitting part II

Figure 3 e: L(f)

Figure 3 f: RL=32 according to high frequency estimation

US 8,173,007 B2

HIGH TEMPERATURE ELECTROCHEMICAL CHARACTERIZATION OF MOLTEN METAL CORROSION

CROSS-REFERENCE TO RELATED APPLICATION

This application claims priority to pending U.S. Provisional Patent Application No. 60/932,098, filed on May 29, 2007. That application is incorporated by reference as if fully rewritten herein.

GOVERNMENT INTEREST

Portions of this invention were made with Government support under Contract No. USDOE-DE-FC36-04GO14038. The Government has certain rights in the invention.

FIELD OF THE INVENTION

This invention relates to a system and method for investigating the corrosion characteristics of molten metal on an alloy in general and the mechanisms of corrosion attack and dross build-up in molten Zn—Al systems in particular.

BACKGROUND

The coating of steel with protective metals such as zinc or aluminum is an economical means of providing corrosion resistance to various grades of steel. Hot dipping of steel is one of the most economical processes for mass production of coated steels and has increased dramatically over the pasta. As a result of this increased demands, the need for greater manufacturing efficiency in the galvanizing process has also gained prominence. Numerous projects have investigated the molten metal corrosion aspects of materials utilized for the submerged pot rolls and other hardware of continuous sheet galvanizing operations. The degradation and frequent failure of these structures results in significant production downtime and leads to high maintenance costs due to extensive repair and replacement.

The corrosion of submerged hardware materials by reacting with molten zinc-aluminum alloy have been studied in the past by analyzing weight loss and dimensional changes. Based on this analysis, an average corrosion rate is calculated. However, the instantaneous corrosion rate of materials attacked by the molten metal has not been analyzed.

Electrochemistry-based measurements aye powerful tools for studying the corrosion behaviors of materials in a service environment. Electrochemistry measurements using water-based solutions, acids, bases, and other chemicals acting as electrolytes at or near room temperature are well known. By analyzing the linear Tafel zone that is one of results of these measurements, the corrosion current density can be calculated and the corrosion rate can be deduced. Conventionally, a variety of electrochemical methods can be used to explore electrochemical reactions at the interface between the metal and an electrolyte solution. However, those methods are limited by the selection of working temperature, usually at or near room temperature (approximately 25° Centigrade (C)), as well as the electrolyte candidates, usually all types of water solutions.

The use of high temperature sensors which utilize electromotive force (EMF) measurements to detect the concentration of a specific component in a certain type of molten metal has been reported. For example, an aluminum sensor that detects the aluminum content in a zinc-aluminum bath, can use a KCl—NaCl liquid operating at about 460° C. as the electrolyte, or, in a subsequent improvement, the eutectic mixture of $MgCl_2$—NaCl—KCl (in a liquid state as a molten salt), with the addition of 2-5 mol % $AlCl_3$ (in liquid state) operating at about 460° C. Using the same principle, an aluminum sensor has been developed using a mixture of NaCl—$AlCl_3$ (liquid) saturated with NaCl (solid) as the electrolyte operating at about 460° C. However, such sensors have a disposable and limited life because the reaction of $AlCl_3$ with moisture or the evaporation of $AlCl_3$ during use. In addition, the current design of aluminum sensors requires a beta-alumina solid electrolyte tube to be inserted into the NaCl—$AlCl_3$ (liquid) saturated with NaCl (solid) electrolyte to prevent diffusion of $ZnCl_2$ (liquid) to the reference electrode. This requirement complicates the sensor design, since an outer tube is required to contain the NaCl—$AlCl_3$ (liquid) saturated with NaCl (solid) electrolyte, making it practically impossible to contain sufficient molten salt electrolyte to run the sensor for, a long time. Moreover, given the large volume required for the aluminum sensor, space restrictions limit the amount of the molten chloride electrolyte that can be used in the sensor. Therefore, current high temperature sensors are not able to carry out the electrochemical tests such as polarization and AC impedance performances.

There is a need for a system and method to study the in-situ behavior of molten metal instant corrosion rates and interfacial performance.

SUMMARY OF THE INVENTION

A system and method of high temperature electrochemical characterization is provided which enables the study of molten metal corrosion of an alloy at high temperatures such as those in the range of 450° C. to 480° C. An alloy sample which is immersed in, and attacked by, the liquid metal melt is used as a working or measuring electrode. A pure form of a particular metal component is used as an auxiliary electrode or counter electrode. The reference electrode or standard electrode is the pure metal component, the selection of which depends on the working electrode. In a two electrode system, the reference electrode works also as the auxiliary electrode, coupled with the working electrode. The reference electrode is insulated by a ceramic sleeve having a micro pinhole provided therein. This pinhole exposes the electrode to the electrolyte through capillary action.

The electrolyte comprises two types of stable high temperature ionic conductors: molten salt and solid β-alumina. A mixture of molten salt of an alkali halide (such as NaCl) and/or an alkaline earth halide (such as $MgCl_2$), together with a halide of the particular metal component (such as $AlCl_3$) is used as the active electrolyte to carry the charges and convert a chemical potential change of the particular metal into a chemical potential change of the alkali or alkaline earth metal. The active substance meets the requirements for a concentration cell, through which the chemical potential of the particular metal component is experimentally detectable when the system equilibrium is built up between a solid phase and a liquid phase.

Another stable high temperature ionic conductor, β-alumina, is also applied to prevent the diffusion of molten metal into contacting the reference electrode and therefore avoid the cell contamination. Pure tungsten is used as the electron leads, which does not react with any element in the experimental system at temperatures as high as 480° C. The reference electrode and the working electrode, an alloy sample immersed in the metal melts, are held by a β-alumina container. The counter electrode is immersed inside the molten salt electrolyte outside the β-alumina container but within a graphite crucible. A furnace having a heating system is connected with a vacuum pump and an argon gas purge tube to prevent oxidation. The electrode feed-through for electronic signal input-output is installed by press fittings on top of the furnace. A control circuit is regulated for generating signals from electrochemical facilities and receiving detection signals from the tested cell. An interface potentiostat/galvanostat connected with an impedance/gain-phase analyzer is used for signaling and data recording. The performance of the concentration cell is mainly determined by the operational temperature, sample dipping duration (corrosion time) in the molten metal bath, and the corrosion reaction rate of the working electrode.

This invention may preferably, but not exclusively, select from the corrosion couples of metal/alloy corroded by molten zinc/aluminum, solder or copper melt.

Various electrochemical experimental methods can be applied such as electrochemical impedance spectroscopy; potentiodynamic polarization, and cyclic voltammetry.

DESCRIPTION OF THE PREFERRED EMBODIMENTS

Figure 1:
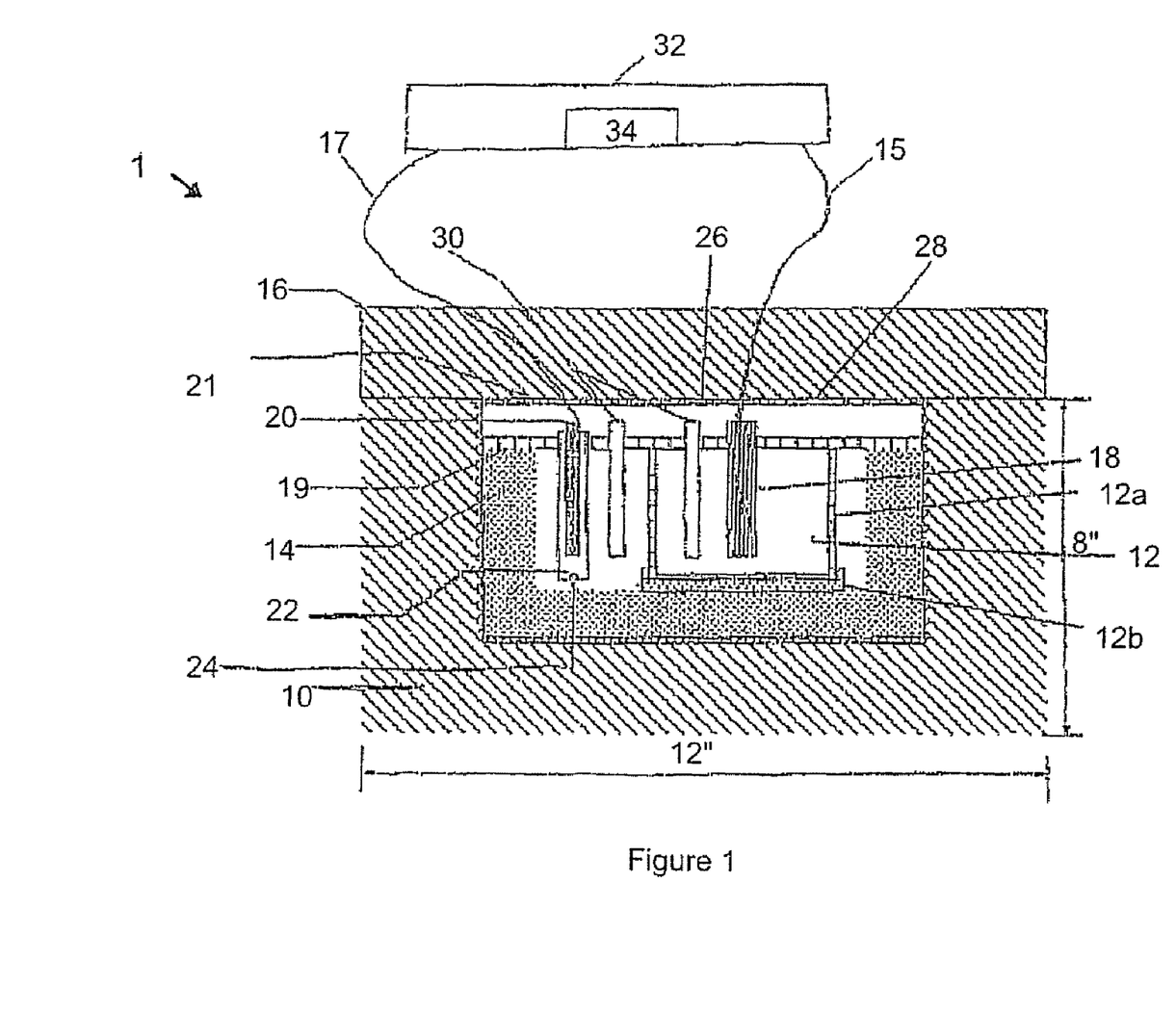
FIG. 1 is a schematic representation of a side view of a preferred embodiment of the system of the present invention.

FIG. 1 shows a schematic of a system 1 for the high temperature (greater than 450° C.) in-situ determination of corrosion characteristics of a molten metal on an alloy under study. FIG. 1 shows a furnace 10 that can be used to measure the corrosion characteristics of a molten metal on an alloy. Furnace 10 includes a crucible 12 (having a side wall 12a, and a bottom 12b) for molten metal and another crucible 14 for molten salt. Crucible 12 is preferably formed of β-alumina and crucible 14 is preferably formed from graphite. Preferably, crucible 12 and crucible 14 are sized so that crucible 12 fits within crucible 14. Furnace 10 preferably has a ceramic fiber insulation and has an insulated cover 16 which rests over top the crucibles 12 and 14.

Alloy sample 18 is inserted into crucible 12 where it is immersed within the molten metal. When coupled to an electrode lead 15 (preferably made of platinum or tungsten, and more preferably tungsten due to cost issues) that passes through the cover 16, alloy sample 18 functions as a working electrode. A solid aluminum electrode 20 that is surrounded by ceramic sleeve 22 is immersed within the molten salt in crucible 14 outside of crucible 12. Another electrode lead 17 (preferably made of platinum) passing through cover 16 enables reference electrode 20 to function as a reference electrode. An opening 24 passing through ceramic sleeve 22 enables the molten salt to contact the reference electrode 20 via capillary action. Preferably opening 24 is a micro sized hole.

Furnace 10 preferably includes a heating system having an argon gas supplier 26 (purge tube), a vacuum pump connection port 28 that allows for a connection to a vacuum pump, and a type K thermocouple 30 having protective alumina sleeves. Furnace cover 16 is equipped with openings for the working electrode, reference electrode (and the counter electrode if provided), and the thermocouple. Preferably, power controllers and temperature controllers (not shown in FIG. 1) assist in the operation of the furnace 10. FIG. 1 shows an exemplary outside furnace dimension of 8 inches (not including the cover 16) by 12 inches. It will be appreciated by those skilled in the art that the furnace of the present invention may be of any desired dimensions and is not limited to the particular dimensions set forth in FIG. 1. As shown in FIG. 1, the other end of each of the electrode leads 15 and 17, respectively, are preferably connected to a electrochemical interface 32 equipped with a computerized corrosion system 34, such as for example a Solartron system that is commercially available. FIG. 1 shows a most preferred embodiment of this invention having an optional interior furnace chamber lid 19 that has multiple openings that allow for the reference and working electrodes and thermocouples to pass through. Preferably lid 19 is made of alumina. FIG. 1 also shows optional cover flange 21.

In one particular embodiment, the molten salt provided in crucible 14 is an electrolyte formed from solid sodium chloride in a saturated sodium chloride-aluminum chloride molten salt. The alloy sample 18 is a 316L stainless steel specimen and the molten metal in crucible 12 is a galvanizing bath formed from molten zinc and aluminum. Pure tungsten is most preferably used as the electrode leads because it does not react with any element in the experimental system at the operating temperatures as high as 480° C. The furnace was connected with a vacuum pump via vacuum pump connection port 28 and an argon gas purge tube 26 to prevent oxidation. In a most preferable embodiment of this invention, the electrode feed-through (electrode leads) for electronic signal input-output are installed by press fittings on top of cover 16.

The present invention provides a system for the high temperature in-situ determination of corrosion characteristics of a molten metal on an alloy under study comprising (a) a furnace; (b) a first crucible provided in the furnace; (c) a reference electrode (working as a counter electrode) formed from a generally pure loan of a generally pure first metal provided in the first crucible; (d) an electrolyte provided in the first crucible, the electrolyte comprising a molten salt of a halide of the first metal; (e) a second crucible provided within the furnace, the second crucible containing a molten metal under study; (f) a measuring electrode formed from an alloy under study, the measuring electrode being immersed in the second crucible; and (g) means to measure the electrochemical effects of corrosion of the molten metal under study on the alloy under study. The system of the present invention further provides wherein the furnace comprises a vacuum pump to withdraw air from the furnace, an argon gas purge tube, and a thermocouple provided within each of the first crucible and second crucible, wherein the furnace is maintained at conditions sufficient to maintain the electrolyte and the molten metal in liquid phase.

In another embodiment of the present invention, the system, as described herein, provides wherein the second crucible is provided within the first crucible and is formed from a material resistant to the electrolyte.

In yet another embodiment of the present invention, the system, as described herein, provides wherein the reference electrode is insulated by a ceramic sleeve, and wherein the reference electrode is exposed to the electrolyte through capillary action through at least one opening provided through the ceramic sleeve.

Another embodiment of the system of the present invention, as described herein, provides wherein the electrolyte further comprises a molten salt of at least one of an alkali halide and an alkaline earth halide and wherein the second crucible is formed from solid β-alumina.

In another embodiment of the system of the present invention, as described herein, the molten metal is formed from zinc-aluminum and the alloy is steel.

Another embodiment of the system of the present invention, as described herein, provides wherein the electrolyte comprises a mixture of sodium chloride and aluminum chloride and the reference electrode is formed from generally pure aluminum and is insulated by a ceramic sleeve, and wherein the reference electrode (working as the auxiliary electrode) is exposed to the electrolyte through capillary action through at least one opening provided through the ceramic sleeve.

In yet another embodiment of the system of the present invention, as described herein, the first crucible is formed from graphite and said second crucible is formed from solid β-alumina.

In another embodiment of the system of the present invention, as described herein, the means to measure by electrochemical means the corrosion effect of the molten metal on the alloy under study performs an analysis using at least one of an electromotive force, potentiodynamic and galvanodynamic polarization, cyclic voltammetry, and electrical impedance spectroscopy to electrochemically measure the corrosion effect.

In a preferred embodiment of this invention, the system of the present invention includes wherein the furnace is operated at temperatures in the range from about 450° C. to about 480° C.

A method for the high temperature in-situ determination of corrosion characteristics of a molten metal on an alloy Linder study is provided comprising the steps of: (a) providing a first crucible in a furnace; (b) inserting a reference electrode formed from a generally pure form of a generally pure first metal in the first crucible; (c) providing an electrolyte in the first crucible, the electrolyte comprising a molten salt of a halide of the first metal; (d) providing a second crucible within the furnace, the second crucible containing a molten metal under study; (e) immersing a measuring electrode formed from an alloy under study in the second crucible; and (f) measuring the electrochemical effects of corrosion of the molten metal under study on the alloy under study.

In another embodiment of the method of the present invention, as described herein, the second crucible is provided within the first crucible and is formed from a material resistant to the electrolyte. Other embodiments of the method of the present invention, as described herein, provide for the further steps of insulating the reference electrode with a ceramic sleeve and providing at least one opening through the ceramic sleeve, the reference electrode being exposed to the electrolyte through capillary action through the opening in the ceramic sleeve.

The method of the present invention as described herein including wherein the electrolyte further comprises a molten salt of at least one of an alkali halide and an alkaline earth halide and wherein the second crucible is formed from solid β-alumina. Preferably, the method includes wherein the molten metal is formed from zinc-aluminum and wherein the alloy is steel.

In another preferred embodiment of the method of the present invention, as described herein, including wherein the electrolyte comprises a mixture of sodium chloride and aluminum chloride and the reference electrode is formed from generally pure aluminum and is insulated by a ceramic sleeve, the reference electrode being exposed to the electrolyte through capillary action through one opening provided through the ceramic sleeve.

The method of the present invention, as described herein, including wherein the means to measure the electrochemical effects of corrosion of said molten metal on said alloy under study performs an analysis using at least one of electromotive force, potentiodynamic and galvanodynamic polarization, cyclic voltammetry, and electrical impedance spectroscopy to electrochemically measure the corrosion effect. In another embodiment, the method includes wherein the furnace is operated at temperatures in the range of from about 450° C. to about 480° C.

EXPERIMENTAL

In-situ high temperature electromotive force (EMF) and high temperature electrochemical tests using an aluminum concentration cell were used to explore the mechanisms of molten zinc/aluminum corrosion and dross formation in galvanizing processes. The nature of dross was observed by determining its nucleation-phase transformation and stability domains in a molten zinc bath as functions of working temperature (T) and immersion time (t). The electrochemical corrosion behavior of an iron-aluminum alloy containing small amount of zinc intermetallic dross particles was also studied.

A Solartron 1287 interface potentiostat/galvanostat connected with a Solartron 1260 impedance/gain-phase analyzer was used for signaling and data recording. Data was analyzed by Solartron CorrWare, Zplot and multiStat software. A laptop computer controlled the entire system. All experiments were performed at temperatures ranging from 450° C. to 480° C. Four experimental methods were applied: (1) electromotive force (EMF), (2) electrochemical impedance spectroscopy (EIS), (3) potentiodynamic and galvanodynamic polarization, and (4) cyclic voltammetry (CV).

The high temperature electrochemical tests were designed to use seven times the amount of molten chloride electrolyte used in a conventional aluminum sensor. The greater supply of electrolyte facilitates ion transfer during the reaction, thus permitting sufficient time to detect the electrochemical and EMF behavior as the high temperature experiment runs.

Zinc melts of about 2 kg, with 0.22 wt % aluminum, were prepared in a graphite crucible to obtain a clean galvanizing bath without iron contamination. High grade zinc ingots supplied by Metallics Systems (Division of Pyrotek Inc.) were used to prepare the zinc bath. A Mother alloy composed of zinc with 5 wt % aluminum, supplied by Wheeling Nisshin Co, was added to the bath as an aluminum source. Analytical grade super high purity (99.999%) aluminum rods were used as the reference electrodes which functioned also as the counter electrode. The working electrode was 316L stainless steel wire. The surface of the 316L stainless steel wire was mechanically polished with sand paper to 800 grit, and then rinsed with distilled water before the experiments started.

The electrolyte was a hypoeutectic mixture of sodium chloride and hydrous aluminum chloride saturated with solid sodium chloride. Since aluminum chloride evaporates easily, the vapor pressure at the experimental temperature was controlled to ensure the composition works well as an ion conductor. Both the sodium chloride and hydrous aluminum chloride were analytical grade pure, and the total mass of salt electrolyte was 1157.45 grams, determined by the size of the graphite crucible used for the tests. Although aluminum chloride is very volatile, it was established that during the experiment, sufficient aluminum chloride remained as the electrolyte to keep the potential steady.

β-Alumina was used in the experiment as the solid electrolyte due to its layered crystal structure, which makes it an excellent ion conductor that is stable in corrosive, reducing and oxidative environments. The whole block of pure β-alumina raw materials were machined down to a cup by using a pair of custom-designed core drills. The wall thickness of the β-alumina cup was 18 mm and the length was 155 mm.

The following is the operating procedure used for the testing process.

1. Performing pure zinc pickling to remove the oxides from the stainless steel wire. The zinc and zinc-5% aluminum alloy pieces were weighed before adding them to the beta-alumina cup (crucible).
2. Inserting the stainless steel wire working electrode and a K type thermocouple through the cover into the pieces of pure zinc and zinc-5% aluminum alloy sitting in the beta-alumina cup. Placing the beta-alumina cup in the center of the graphite crucible.
3. Inserting a bent aluminum rod as a reference electrode, which circle around the beta-alumina cup. Using aluminum chloride and sodium chloride to fill up the space between alumina cup and graphite crucible.
4. Covering the crucible with the cover. Wiring one end of each of the working and reference electrodes with one end of separate electrode leads (preferably platinum leads), respectively, inside the furnace and inserting the other end of each electrode lead, respectively, through the furnace cover.
5. Placing the furnace cover over the furnace and fastening those two parts for establishing a secure connection of the furnace covet to the furnace.
6. Connecting the other end of each of the electrode leads, respectively, that extend through the cover, to an electrochemical interface, such as for example a Solartron equipped with a computerized corrosion system. Hooking up the thermocouples with a temperature-power controller box.
7. Installing a vacuum pump to the vacuum pump connector port. Checking the vacuum for leaks. Checking the argon gas pressure/amount and checking for leakage.
8. Evacuating the sealed furnace chamber to a vacuum of $1 \times 10^2$ Pa and then refilling with purified argon gas to a pressure of $1 \times 10^5$ Pa (1 atm or 15 psi).
9. Following evacuation and refilling, heating the furnace chamber to 465° C. at a rate of 5.6° C. per minute and the starting to detect the potential with no current input (i=10E−10A)
10. Stabilizing the whole system at 465° C. for 120 minutes to melt the zinc-aluminum galvanizing solution and the aluminum chloride-sodium chloride molten salt after establishment of equilibrium.
11. Quickly performing EIS at open circuit potential ($10^5$ Hz to $10^1$ Hz) and then remaining at this temperature and performing EMF—time plots.
12. Increasing temperature from 465° C. to 480° C. and performing EIS at open circuit potential, and then measuring EMF for 30 mins (minutes).
13. Increasing temperature from 480° C. to 500° C. and performing EIS at open circuit potential and then measuring EMF for 30 mins.
14. Increasing temperature from 500° C. to 515° C. and performing EIS at open circuit potential, and then measuring EMF potential for 30 mins.
15. Decreasing temperature from 515° C. to 455° C. and performing EIS at open circuit potential, and then measuring EMF potential for 30 mins.
16. Decreasing temperature from 455° C. to 440° C. and performing EIS at open circuit potential, and then measuring EMF potential for 30 mins.
17. Increasing temperature from 440° C. to 465° C. and performing a potential polarization curve (scanning potential from 0.22 V to 1.78 V, scanning rate is 0.5 mV/s).
18. Removing the Solartron and lifting up the furnace cover with the thermocouples. Disconnecting the feedthrough (electrode leads). Removing the stainless steel wire and an aluminum rod and ceramic tubes used to protect the thermocouples.
19. Removing the beta-alumina cup from the molten aluminum chloride-sodium chloride salt and pouring out the molten zinc followed by putting it upside down to clear any remaining molten zinc.
20. Removing the crucible with molten salt from the furnace and pouring out the molten salt followed by putting it upside down to clear molten salt.
21. Placing a stainless plate or tray back into the furnace and then placing the beta-alumina cup back on this stainless tray.
22. Covering the furnace so that the thermocouple (which is mounted in the furnace lid) can detect the furnace PV temperature. Increase SP to 465° C. for 60 mins.
23. Reducing SV to stabilized 370° C.→315° C.→260° C.→200° C.→150° C.→90° C.→25° C. (about room temp).
24. Uncovering the furnace to remove the beta-alumina cup and cleaning it with acid.

After the experiment is finished, the 316L stainless steel wire sample is taken out, and a cross-section of the rods is cut at the dross line using EDM. The sections are then mounted and polished for analysis with scanning electron microscopy and energy dispersive spectroscopy.

Electromotive Force (EMF)

EMF has been used in many molten metal research studies such as liquid Li—Sn system. By employing the in-situ electromotive force (EMF) method using an aluminum concentration cell, the chemical potential of $Al(\mu_{Al})$ in the galvanizing bath, coexisting with solid dross phase, can be experimentally determined as a function of temperature (T). The potential diagram can be estimated to illustrate the nucleation and stability domains of the dross phase in the molten Zn bath as functions of working temperature (T) and immersion time (t). Most of the reaction kinetics of dross nucleation are categorized as a heterogeneous precipitation and phase transformation, which are controlled, to a large extent, by the supersaturation. Based on the established EMF—T and EMF—t plots, it was possible to determine the critical supersaturation boundary for dross nucleation and phase transformation and therefore experimentally evaluate and illustrate the behaviors of dross.

During the EMF tests, 316L stainless steel dipped in liquid Zn-0.22 wt % Al was the working electrode, while aluminum with 99.999% purity was the reference electrode. The electrolyte was (NaCl+AlCl$_3$) molten salt saturated solid NaCl. These tests showed that during the rapid temperature drops, the corresponding EMF value dropped abruptly, which caused more aluminum transfer from liquid phase to solid phase, which resulted in the drop of the EMF value. Similarly, adding more aluminum to the testing system raised the aluminum content in the solid phase, and therefore, reduced the EMF Potentiodynamic and Galvanodynamic Polarization The anodic potentiodynamic and galvanodynamic polarization, with a scanning rate of 0.5 mV/s and 0.625 mA/s respectively, were carried out on the ($AlCl_3$—NaCl) molten salt based 316L+molten Zn-0.22Al system. Anodic potentiodynamic polarization was carried out at temperatures of 455° C. and 475° C. respectively. The polarization began with a potential of −0.22 V (vs. OC), and ended with a potential at +1.78 V (vs. $\dot{E}^0$). For the anodic galvanodynamic polarization, the polarization began with a current of −0.50 A and ended with a current at +1.0 A at 485° C. Electrochemical potentiodynamic polarization curves were measured and recorded using Solartron 1287 interface potentiostat/galvanostat controlled by Solartron, CorrWare and multiStat software.

Figure 2:
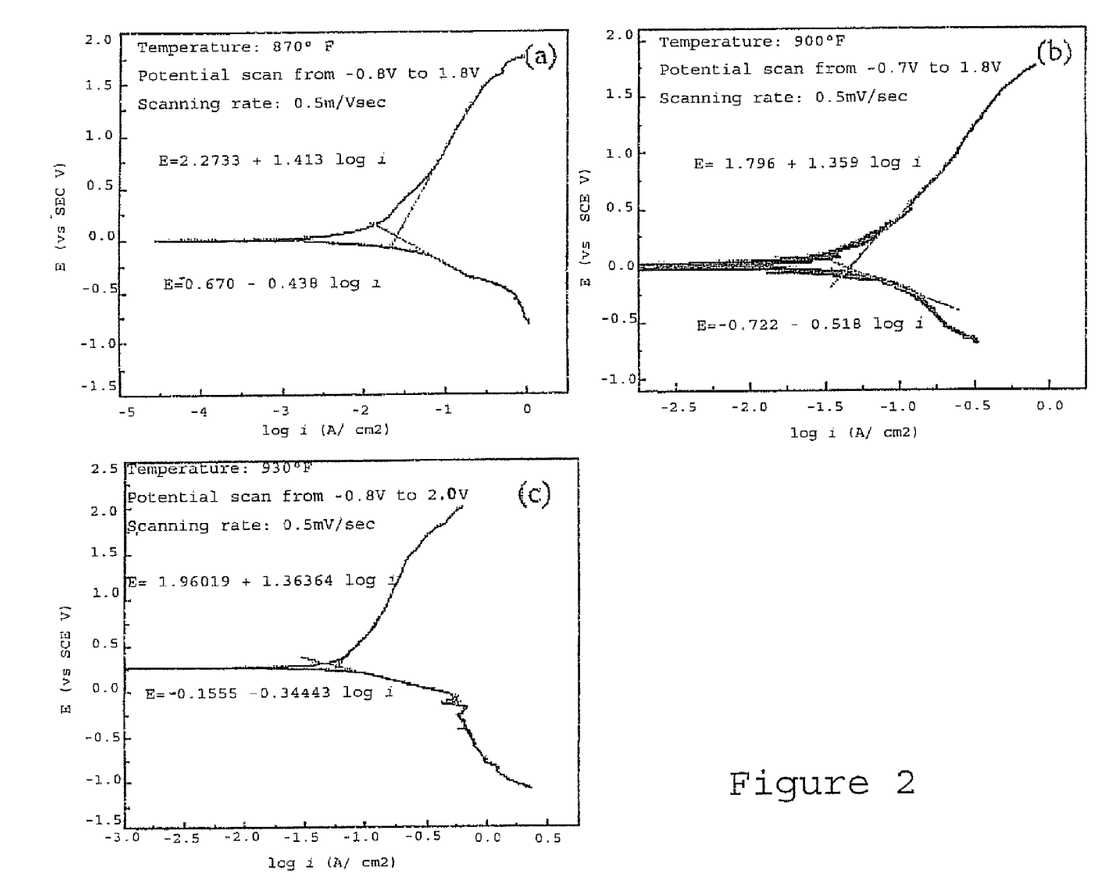
FIGS. 2(a)-2(c) show the potentiodynamic polarization results obtained by applying the system of the present invention to a sample.

FIGS. 2(a)-2(c) show the potentiodynamic polarization results obtained by using the system and method of the present invention. Based on the polarization curves, the exchange current density ($i_{corr}$), which represents the instant corrosion rate, was calculated by combining the Tafel lines. The amount of the transferred electrons (n) in the dominating step of the redox couple was also deduced. In detail, the calculated results of $i_{corr}$ values are as follows.

465° C.: Ecorr=0.231 V; $i_{corr}$=$10^{-1.590}$ A; na=0.212
480° C.: Ecorr=0.195 V; $i_{corr}$=$10^{-1.342}$ A; na=0.221
500° C.: Ecorr=0.261 V; $i_{corr}$=$10^{-1.240}$ A; na=0.22 where Ecorr is the zero charge potential and na is the charge transfer number in the anodic process.

Cyclic Voltammetry

Besides the polarization described above, cyclic voltammetry was also applied to the ($AlCl_3$—NaCl) molten salt based (316L+molten Zn-0.22Al) electrochemistry system. Cyclic voltammetric experiments were carried out using a Solartron SI 1287 electrochemical interface equipped with a computerized corrosion system (Solartron). The automatic "current interrupt" method included in the Solartron operational software was employed to compensate for any undesired ohmic drop caused by the distance between the working, reference, and counter electrodes. In the "current interrupt" technique, the cell current is periodically turned off for a short time period. With no current through the solution resistance, the undesired ohmic drop disappears. The potential drops at the electrode surface remains constant on a rapid time scale. The difference in potential with the current flowing and without is a measure of the uncompensated undesired ohmic drop. The scanning potential range was between −0.60 V and +0.40V (vs SCE). The scanning rate was 50 mV $s^{-1}$. The experiment was running at 500° C.

Electrochemical Impedance Spectroscopy (EIS or AC Impedance)

EIS measurements were performed by applying an AC signal of amplitude (AC=20 mV) with and without external DC polarization (DC=500 mV). The scanning frequency range used was from $10^6$ to $10^{-1}$ Hz. A Solartron 1260 impedance gain-phase analyzer controlled by Solartron ZWare & multiStat software was applied. All the data were recorded 30 points per decade, averaged over 5 seconds at each frequency. All experiments were run at temperatures ranging from 455° C. to 515° C.

Figure 3:
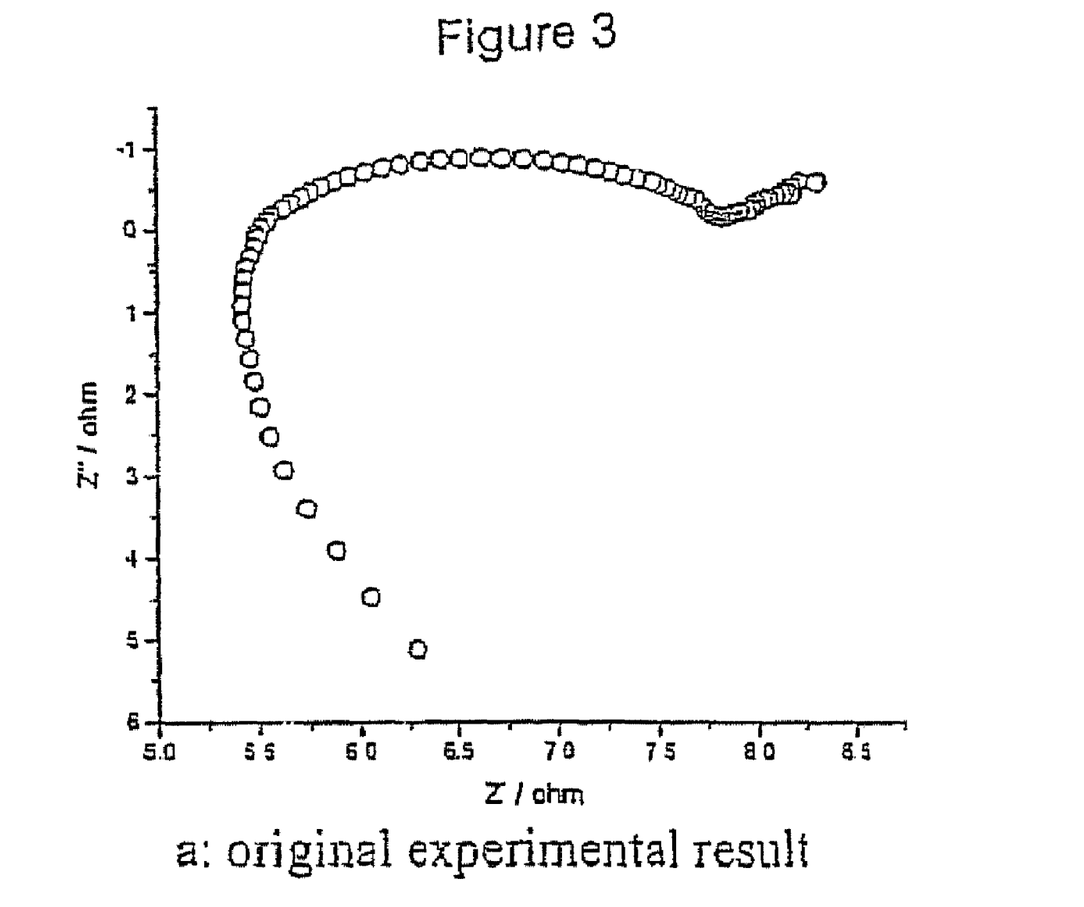
FIG. 3 shows the results of electrochemical impedance spectroscopy to molten metal corrosion of a sample studied using the system of the present invention.

All the EIS data are plotted in FIG. 3. An influence of the external DC polarization is clear by comparing the six EIS curves. Typically, applying DC polarization decreased the value of the $Z_F$, shifting the EIS curves towards the negative direction of the $Z_F$ axis. Since $Z_F$ was mainly determined by the value of the constant charge transfer resistance, the external DC polarization accelerated the whole cell reaction rate by reducing the value of the charge transfer resistance (or so-called electrode reaction resistance).

The development of more than one time constant is deduced from inspection of the EIS spectra, shown in FIG. 3. The result reflects the diversity of phenomena that occur in the systems under investigation. The HIS plot is divided into three zones: (i) inductance in the high frequency zone, (ii) capacitance in the middle frequency zone, and (iii) the Warburg resistance in the low frequency zone with linear slope very close to 1, which implies a standard Warburg resistance determined by the system diffusion.

The present invention can be used to conduct research on molten zinc/aluminum corrosion and dross formation thermodynamics by applying electrochemistry research methods at high temperature. Nucleation and stability of dross phases in equilibrium with the liquid phase can be investigated. Using the present invention, all regular electrochemical techniques and measurements, including polarization, impedance, and cyclic voltammetry, can be used to study high-temperature corrosion and dross formation by increasing the working temperature of the molten metal corrosion system.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples. It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

We claim:

1. A system for the high temperature in-situ determination of corrosion characteristics of a molten metal on an alloy under study comprising:
   a. a furnace, wherein said furnace is operated at temperatures in the range of about 450 degrees Centigrade to about 480 degrees Centigrade;
   b. a first crucible provided in said furnace;
   c. a reference electrode formed from a generally pure form of a generally pure first metal provided in said first crucible;
   d. an electrolyte provided in said first crucible, said electrolyte comprising a molten salt of a halide of said first metal;
   e. a second crucible provided within said furnace, said second crucible comprising a solid electrolyte, and wherein said second crucible is suitable for containing a molten metal under study; wherein said molten electrolyte and said solid electrolyte are each ionic conductors;

f. a measuring electrode formed from an alloy under study, said measuring electrode being immersed in said second crucible; and g. means to measure exchange current density and transferred electrons by electrochemical means for determining the corrosion effect of said molten metal under study on said alloy under study.

2. The system of claim 1 wherein said furnace comprises a vacuum pump to withdraw air from said furnace, an argon gas purge tube, and a thermocouple provided within each of said first crucible and second crucible, wherein said furnace is maintained at conditions sufficient to maintain said electrolyte and said molten metal in liquid phase.

3. The system of claim 1 wherein said second crucible is provided within said first crucible and is formed from a material resistant to said electrolyte.

4. The system of claim 1 wherein said reference electrode is insulated by a ceramic sleeve, said reference electrode being exposed to said electrolyte through capillary action through an opening provided through said ceramic sleeve.

5. The system of claim 1 wherein said electrolyte further comprises a molten salt of at least one of an alkali halide and an alkaline earth halide and wherein said second crucible is formed from solid β-alumina.

6. The system of claim 1 wherein said molten metal is formed from zinc-aluminum and said alloy is steel.

7. The system of claim 6 wherein said electrolyte comprises a mixture of sodium chloride and aluminum chloride and said reference electrode is formed from generally pure aluminum and is insulated by a ceramic sleeve, said reference electrode being exposed to said electrolyte through capillary action through an opening provided through said ceramic sleeve.

8. The system of claim 7 wherein said first crucible is formed from graphite and said second crucible is formed from solid β-alumina.

9. The system of claim 1 wherein said means to measure by electrochemical means the corrosion effect of said molten metal on said alloy under study performs an analysis using at least one of electromotive force, potentiodynamic and galvanodynamic polarization, cyclic voltammetry, and electrical impedance spectroscopy to electrochemically measure the corrosion effect.

10. A method for the high temperature in-situ determination of corrosion characteristics of a molten metal on an alloy under study comprising the steps of:

a. providing a first crucible in a furnace, said furnace being operated at temperatures in the range of about 450 degrees Centigrade to about 480 degrees Centigrade;

b. inserting a reference electrode formed from a generally pure form of a generally pure first metal in said first crucible;

c. providing an electrolyte in said first crucible, said electrolyte comprising a molten salt of a halide of said first metal;

d. providing a second crucible within said furnace, said second crucible comprising a solid electrolyte, and wherein said second crucible is suitable for containing a molten metal under study; wherein said molten electrolyte and said solid electrolyte are each ionic conductors;

e. immersing a measuring electrode formed from an alloy under study in said second crucible; and f. measuring an exchange current density and transferred electrons for determining the corrosion effect of said molten metal under study on said alloy under study.

11. The method of claim 10 including wherein said second crucible is provided within said first crucible and is formed from a material resistant to said electrolyte.

12. The method of claim 10 including comprising the further steps of insulating said reference electrode with a ceramic sleeve and providing an opening through said ceramic sleeve, said reference electrode being exposed to said electrolyte through capillary action through said opening in said ceramic sleeve.

13. The method of claim 10 including wherein said electrolyte further comprises a molten salt of at least one of an alkali halide and an alkaline earth halide and wherein said second crucible is formed from solid β-alumina.

14. The method of claim 10 including wherein said molten metal is formed from zinc-aluminum and said alloy is steel.

15. The method of claim 14 including wherein said electrolyte comprises a mixture of sodium chloride and aluminum chloride and said reference electrode is formed from generally pure aluminum and is insulated by a ceramic sleeve, said reference electrode being exposed to said electrolyte through capillary action through an opening provided through said ceramic sleeve.

16. The method of claim 15 including wherein said first crucible is formed from graphite and said second crucible is formed from solid β-alumina.

17. The method of claim 10 including wherein said means to measure by electrochemical means the corrosion effect of said molten metal on said alloy under study performs an analysis using at least one of electromotive force, potentiodynamic and galvanodynamic polarization, cyclic voltammetry, and electrical impedance spectroscopy to electrochemically measure the corrosion effect.

* * * * *